(12) United States Patent
Kalbe et al.

(10) Patent No.: US 6,566,348 B1
(45) Date of Patent: May 20, 2003

(54) PESTICIDES BASED ON CYCLIC POLYSILOXANES

(75) Inventors: Jochen Kalbe, Leichlingen (DE); Andreas Turberg, Haan (DE); Michael Londershausen, Erkrath (DE); Norbert Mencke, Leverkusen (DE); Reiner Pospischil, Bergheim (DE); Rainer Sonneck, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 582 days.

(21) Appl. No.: 09/077,119

(22) PCT Filed: Nov. 18, 1996

(86) PCT No.: PCT/EP96/05059

§ 371 (c)(1), (2), (4) Date: May 21, 1998

(87) PCT Pub. No.: WO97/19596

PCT Pub. Date: Jun. 5, 1997

(30) Foreign Application Priority Data

Nov. 30, 1995 (DE) .......... 195 44 669

(51) Int. Cl.$^7$ .......... A61K 31/695; C07F 7/21; C07F 7/08; C07F 7/04
(52) U.S. Cl. .......... 514/63; 556/460; 556/462
(58) Field of Search .......... 514/63; 556/460, 556/462

(56) References Cited

U.S. PATENT DOCUMENTS 4,654,328 A * 3/1987 Itoh et al. .......... 514/63

FOREIGN PATENT DOCUMENTS

EP 191543 * 8/1986

* cited by examiner

Primary Examiner—James O. Wilson
Assistant Examiner—Everett White
(74) Attorney, Agent, or Firm—Joseph C. Gil; Richard E. L. Henderson

(57) ABSTRACT

The present invention relates to immediately acting pest control compositions based on cyclic polysiloxanes, which can be employed without a residue and without a lasting action.

6 Claims, No Drawings

PESTICIDES BASED ON CYCLIC POLYSILOXANES

The present invention relates to immediately acting pest control compositions based on cyclic polysiloxanes which can be employed without a residue and without a lasting action.

It was known that cyclic polysiloxanes having 4 and 5 siloxane units are insecticidally active. It was also known that insects can be killed by spraying using polysiloxanes (U.S. Pat. No. 4 654 328).

Use in practice shows, however, that problems occur during use. Cyclic polysiloxanes having 4 siloxane units crystallize out at temperatures below about 18° C. and can then no longer be sprayed without problems. No satisfactory action results from spraying insects with cyclic polysiloxanes from aerosol sprays which produce an average droplet size of 50μ.

The invention therefore relates to the following mixtures and compositions:

1. Immediately acting insecticidal and acaricidal composition which can be used without a residue and without a lasting action and is based on cyclic polysiloxanes of the formula (I)

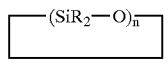

in which
R represents identical or different radicals from the group consisting of methyl, ethyl and propyl,
n represents integers from 3 to 6,
which are sprayed onto the pests in the customary manner with an average droplet size in the spray mist of 130 to 500μ (diameter).

2. Composition according to point 1 (above), characterized in that it predominantly comprises, as the constituent of the formula (I), compounds in which the index n is 5.

3. Mixture of cyclic polysiloxanes of the formula (I)

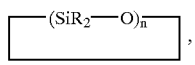

in which
R represents identical or different radicals from the group consisting of methyl, ethyl and propyl,
n represents integers from 3 to 6,
characterized in that the constituents of the formula (I) with the indices 4 and 5 is present in the weight ratio n=4<85% (weight)
n=5>15% (weight).

4. Mixture according to point 3 (above), characterized in that the constituents of the formula (I) with the indices 4 and 5 are present in the weight ratio n=4 85 to 50% by weight
n=5 15 to 50% by weight.

5. Mixture according to point 3 (above), characterized in that the constituents of the formula (I) with the indices 4 and 5 are present in the weight ratio n=4 80 to 60% by weight
n=5 20 to 40% by weight.

6. Mixture according to point 3 (above), characterized in that the constituents of the formula (I) with the indices 4 and 5 are present in the weight ratio n=4 75% by weight
n=5 25% by weight.

The compositions according to the invention have considerable advantages for practical use. Their action on pests starts immediately, i.e. the user sees the success of the control measure directly. The active compound acts exclusively in direct contact with the pest, and preventive treatment (residual action) is not possible. The compositions are used only during an acute attack and only directly on the pests to be controlled. That is to say, no preventive and superfluous amounts of active compound are spread into the environment.

Beneficial organisms can be protected by the controlled use. The active compound is non-toxic to plants, mammals and humans.

The active compound evaporates rapidly from surfaces affected (plants, furniture, walls, window panes), without leaving behind residues.

The active compound is degraded abiotically within a short time by the action of light.

The compositions according to the invention are suitable for controlling animal pests, preferably arthropods, in particular insects and arachnids, which are encountered in agriculture, in forestry, in the protection of stored products and of materials, and in the field of hygiene. They are active against normally sensitive and resistant species and against all or some stages of development.

The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypodermna spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The compositions are suitable for controlling animal pests, such as arthropods, preferably insects and arachnids, encountered in animal husbandry and animal breeding of stock, breeding, zoo, laboratory and test animals and pets, and have favorable toxicity to warm-blooded animals. They are active here against all or some stages of development of the pests and against resistant and normally sensitive species of the pests.

The pests include:

From the order of the Anoplura, for example, Haematopinus spp., Linognathus spp., Solenopotes spp., Pediculus spp. and Pthirus spp.;

From the order of the Mallophaga, for example, Trimenopon spp., Menopon spp., Eomenacanthus spp., Menacanthus spp., Trichodectes spp., Felicola spp., Damalinea spp. and Bobiola spp.;

From the order of the Diptera, for example, Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cardylobia spp., Cochiomyia spp., Chrysomyia spp., Sarcophaga spp., Wohlfartia spp., Gaserophilus spp., Oesteromyia spp., Oedemagena sp., Hypoderma spp., Oestrus spp., Rhinoestrus spp., Melophagus spp. and Hippobosca spp.

From the order of the Siphonaptera, for example, Ctenocephalides spp., Echidnophaga spp. and Ceratophyllus spp.

From the order of the Metastigmata, for example, Hyalomma spp., Rhipicephalus spp., Boophilus spp., Ambyomma spp., Haemophysalis spp., Dermacentor spp., Ixodes spp., Argas spp., Ornithodorus spp. and Otobius spp.; from the order of the Mesastigmata, for example, Dermanyssus spp., Ornithonyssus spp. and Pneumonyssus spp.

From the order of the Prostigmata, for example, Cheyletiella spp., Psorergates spp., Myobia spp., Demdex spp. and Neotrombicula spp.;

The domestic and stock animals include mammals, such as, for example, cattle, sheep, goats, horses, pigs, dogs, cats, camels, water buffalo, donkeys, rabbits, fallow deer and reindeer, fur-bearing animals, such as, for example, mink, chinchilla and racoons, and birds, such as, for example, chickens, turkeys, pheasants, geese and ducks.

The laboratory and test animals include, for example, mice, rats, guineapigs, golden hamsters, dogs and cats.

The pets include, for example, dogs and cats.

The compositions according to the invention can particularly preferably be employed in closed rooms, such as flats, halls or the like. They are particularly suitable for controlling animal pests and nuisances which occur in the home.

In this context, there may be mentioned in particular flies, mosquitoes, wasps, ants, cockroaches and silverfish.

Formula (I) provides a general definition of the cyclic polysiloxanes.

Compounds of the formula (I) in which R represents methyl and n represents 4 and 5 are particularly preferred.

The cyclic polysiloxanes octamethylcyclotetrasiloxane and decamethylcyclopentasiloxane and their mixtures with one another and with cyclic polysiloxanes which are contained in them due to the preparation process may be mentioned in particular.

As already mentioned, the compositions according to the invention are sprayed directly on the pests or nuisances to be controlled. This is effected in the customary manner with pump sprays, aerosol sprays and spraying and atomizing apparatuses.

A prerequisite for successful treatment is an average droplet size of the active compound mist of 130 to $500\mu$ (diameter). The distribution of the droplet size is between 100 and $700\mu$, and 90% of all drops here are smaller than $600\mu$. The spraying and atomizing apparatuses must be constructed such that they guarantee this droplet size.

Only this droplet size guarantees that the pests are affected by an adequate amount of active compound with normal handling (spraying from a distance of about 20 to 100 cm). For example, it has been found that spraying with the active compounds of average droplet size <80$\mu$ at a distance of 60 cm had no action at all on flies.

A distribution of the droplet sizes from 150 to 500$\mu$, where 90% of all drops are <420$\mu$, is preferred. This corresponds to a mean droplet size of 160 to 300$\mu$.

Decamethylcyclopentasiloxane is particularly suitable as the active compound and agent. This active compound is stable at low temperatures, without crystallizing out, and is therefore easy to store and use.

It is employed, in particular, if stability to low temperatures is important and rapid residue-free evaporation of the active compound plays a minor role.

Mixtures of octamethylcyclotetrasiloxane and decamethylcyclopentasiloxane are particularly preferred if the content of the pentasiloxane is >15% (weight). Such mixtures have the advantage of a good stability toward crystallizing out at low temperatures, associated with rapid residue-free evaporation of the mixture from the surfaces affected. This makes such mixtures particularly suitable for use in the home.

The cyclic polysiloxanes are particularly preferably used as such, without further additions, such as solvents, in the compositions according to the invention.

However, it is easily possible to add the customary additives, such as solvents, surfactants and perfume oils, to the compositions.

EXAMPLE A

Test with Flies (*Musca domestica*)—Spry Method

Test animals: adult *Musca domestica*, Reichswald strain (multiresistant)

Solvent: not applicable

To produce a suitable formulation, 25 parts of decamethylcyclopentasiloxane are mixed with 75 parts of octamethylcyclotetrasiloxane.

100 ml of this active compound preparation are transferred to spray bottles with nozzle diameter. Wire gauze disks of 10.8 cm diameter are introduced (curved hemispherically toward the base) into PP containers (Ø9.7 cm, H 8 cm). 20 flies are stunned with $CO_2$ and transferred to the gauze. The container is closed with a second wire gauze disk, in this case curved upward, and kept at room temperature for 30 minutes until all the flies show normal activity again. The container is held horizontally at a distance of 15 cm from the spray head of the spray bottle. By operating the spray lever 3 times, a total of 3 ml of active compound preparation are sprayed onto the flies. The vessel is then placed with the opening at the top again.

After 1 minute, 100% of the flies were dead.

EXAMPLE B

*Musca domestica/Stomoxys calcitrans*
(Experimental Treatment Under Conditions in Practice in a Pigsty)

The test was carried out in a pigsty. 3 pens in which there were a total of 6 animals were occupied in the sty. The fly infestation was 50–100 flies per animal.

Method

The formulation described in Example A was applied undiluted under a pressure of 4.5 mbar. (Nozzle: Holder series nozzle "Merkur" of brass with a swirl body, nozzle bore 1.5 mm: spray angle about 65°). The spray pressure was regulated via a breathing air bottle.

Only the regions of the sty where there were larger accumulations of flies were sprayed (*M. domestica* and *S. calcitrans*). The amount applied was 30 to 50 g of formulation per m².

Flies which were affected and wetted by the spray mist fell to the floor or remained suspended on the wall or the animals directly after the treatment. No recovery was observed. *M. domestica* and *S. calcitrans* were affected by the spray composition in the same manner.

EXAMPLE C

The formulation described in Example A was applied undiluted with various spray and misting apparatuses (see Table 1) in 2 stables where flies (*M. domestica*) had previously been released (5 000 to 10 000 per room).

TABLE 1

| Application | *Musca domestica* |
|---|---|
| Spray apparatus according to Example B, 4–5 bar, fine nozzle | + + |
| ULV (ROFA) | – |
| Cold mist (Microjet) | – |

+ + = good action
– = no action

The Rofa apparatus is used for ULV application and is distinguished by a distribution of the particular formulation in very fine droplets (5 to 30μ). The fine droplets are not sufficient to achieve an adequate action, even if the animals are sprayed over a relatively long period of time.

The same applies to the cold mist apparatus "Mikrojet", which distributes the substance with an average droplet size of <80μ.

Tests with the apparatus described in Example B again led to the result described. Flies which were affected directly by the droplets died within 15 minutes.

The spray coating was no longer detectable on the walls (lime sandstone) after about 15 minutes,

EXAMPLE D

A plant heavily infested with aphids was sprayed using the pressurized spray apparatus. The aphids affected by the spray mist could be shaken off from the plant within 5 minutes after the treatment and did not recover.

What is claimed is:

1. A method for controlling insects and arachnids comprising the step of spraying a composition comprising at least one cyclic polysiloxane of the formula (I)

$$[-(SiR_2-O)_n-] \quad (I)$$

wherein
R represents identical or different radicals selected from the group consisting of methyl, ethyl and propyl, and
n represents integers from 3 to 6, onto the pests, wherein the droplets in the spray mist have an average diameter of from about 130 to about 500μ.

2. The method of claim 1 wherein the composition comprises a mixture of cyclic polysiloxanes of the formula (I)

$$[-(SiR_2-O)_n-] \quad (I)$$

wherein
R represents identical or different radicals selected from the group consisting of methyl, ethyl and propyl,
n represents integers from 3 to 6,
wherein the constituents of the formula (I) with the indices 4 and 5 are present in the weight ratio
n=4, <85% by weight, and
n=5, >15% by weight.

3. The method of claim 2 wherein the constituents of the formula (I) with the indices 4 and 5 are present in the weight ratio n=4, 50 to 85% by weight, and n=5, 15 to 50% by weight.

4. The method of claim 2 wherein the constituents of the formula (I) with the indices 4 and 5 are present in the weight ratio n=4, 60 to 80% by weight, and n=5, 20 to 40% by weight.

5. The method of claim 2 wherein the constituents of the formula (I) with the indices 4 and 5 are present in the weight ratio n=4, 75% by weight and n=5, 25% by weight.

6. The method of claim 1 wherein the composition comprises predominantly cyclic polysiloxanes in which n=5.

* * * * *